United States Patent
Razavi

(10) Patent No.: US 8,961,417 B2
(45) Date of Patent: *Feb. 24, 2015

(54) CATHETER WITH ELECTRODES FOR IMPEDANCE AND/OR CONDUCTION VELOCITY MEASUREMENT

(75) Inventor: Mehdi Razavi, Houston, TX (US)

(73) Assignee: Texas Heart Institute, Houston, TX (US)

( * ) Notice: Subject to any disclaimer, the term of this patent is extended or adjusted under 35 U.S.C. 154(b) by 1486 days.

This patent is subject to a terminal disclaimer.

(21) Appl. No.: 12/348,695

(22) Filed: Jan. 5, 2009

(65) Prior Publication Data

US 2009/0177069 A1 Jul. 9, 2009

Related U.S. Application Data

(60) Provisional application No. 61/019,131, filed on Jan. 4, 2008.

(51) Int. Cl.
*A61B 5/053* (2006.01)
*A61B 5/042* (2006.01)

(52) U.S. Cl.
CPC ................. *A61B 5/042* (2013.01); *A61B 5/053* (2013.01)
USPC .......................................... 600/371; 600/547

(58) Field of Classification Search
None
See application file for complete search history.

(56) References Cited

U.S. PATENT DOCUMENTS

| | | | |
|---|---|---|---|
| 5,397,340 A | 3/1995 | Nyman | |
| 5,429,130 A | 7/1995 | Goldman | |
| 5,733,323 A | 3/1998 | Buck et al. | |
| 5,876,353 A | 3/1999 | Riff | |
| 6,076,015 A | 6/2000 | Hartley et al. | |
| 6,351,667 B1 | 2/2002 | Godie | |
| 6,512,949 B1 | 1/2003 | Combs et al. | |
| 6,714,814 B2 | 3/2004 | Yamada et al. | |
| 7,226,422 B2 | 6/2007 | Hatlestsad et al. | |
| 7,340,296 B2 | 3/2008 | Stahmann et al. | |
| 7,387,610 B2 | 6/2008 | Stahmann et al. | |
| 8,366,615 B2 | 2/2013 | Razavi | |
| 8,483,821 B2 | 7/2013 | Averina et al. | |
| 2003/0055461 A1 | 3/2003 | Girouard et al. | |
| 2003/0212373 A1 | 11/2003 | Hall et al. | |
| 2005/0277912 A1 | 12/2005 | John | |
| 2005/0288726 A1 | 12/2005 | Gollasch et al. | |
| 2006/0041280 A1 | 2/2006 | Stahmann et al. | |
| 2008/0255470 A1* | 10/2008 | Hauck et al. | 600/547 |
| 2008/0300504 A1 | 12/2008 | Lefkov et al. | |
| 2008/0312645 A1 | 12/2008 | Drasler et al. | |
| 2009/0171235 A1* | 7/2009 | Schneider et al. | 600/547 |

OTHER PUBLICATIONS

You, Fusheng et al., Abstract of "Monitoring Retroperitoneal Bleeding Model of Piglets by Elect Impedance Tomography," Engineering in Medicine and Biology Society, 2008, EMBS 2008, 30th Annual International Conference of the IEEE, Found at: http://ieeexplore.ieee.org/xpl/freeabs_all.jsp?arnumber=4649374, 1 page.

Wikipedia reference for Electrical Impedance Tomography (EIT), Found at: http://en.wikipedia.org/wiki/Electrical_impedance_tomography, 4 pages, 2008.

* cited by examiner

*Primary Examiner* — Celine Qian
(74) *Attorney, Agent, or Firm* — Conley Rose, P.C.

(57) ABSTRACT

An apparatus comprises a catheter comprising a first electrode. The apparatus also comprises a second electrode electrically attached to a person and coupled to the first electrode via the person's tissue. Logic is coupled to the electrodes and generates an electrical signal that is provided through the electrodes and computes an impedance or conduction velocity associated with the electrodes based on the electrical signal. The logic stores a threshold against which said computed impedance or conduction velocity is compared by said logic.

12 Claims, 5 Drawing Sheets

CATHETER WITH ELECTRODES FOR IMPEDANCE AND/OR CONDUCTION VELOCITY MEASUREMENT

CROSS-REFERENCE TO RELATED APPLICATIONS

This application claims priority to provisional application Ser. No. 61/019,131 entitled "Method, System, and Device for Detection of Pericardial Blood or Fluid" and incorporated herein by reference.

STATEMENT REGARDING FEDERALLY SPONSORED RESEARCH OR DEVELOPMENT

Not applicable

BACKGROUND

1. Field of the Disclosure

This invention relates generally to the field of medical devices. More specifically, the invention relates to a method and device using impedance for the detection of fluid (e.g., blood) bleeding such as pericardial effusion, retroperitoneal effusion, etc.

2. Background Information

Radiofrequency ablation (RF ablation) or other invasive cardiac procedures which involve operation within the cardiac chambers, coronary arteries or the heart's venous anatomy have saved many lives. These procedures often involve percutaneous access into the cardiac chambers or epicardial arterial or venous vessels. Catheter, pacing lead, sheath, or other types of device manipulations frequently are performed as key parts of these procedures. Example of this include balloon angioplasty or stent placement. Often, catheter access to the femoral artery is needed.

A rare but potentially dangerous complication of these and similar procedures is inadvertent perforation of a cardiac chamber or an epicardial vessel. Retroperitoneal bleeding is also possible at the site of the insertion of the catheter into the femoral artery. Perforations of a cardiac chamber or an epicardial vessel may lead to accumulation of blood (or other fluids) in the pericardial space or sac. This condition is referred to pericardial effusion. Cardiac tamponade is the patho-physiologic state wherein accumulation of blood or other fluid in the pericardial space or sac leads to impaired filling of the heart and a secondary decrease in cardiac output and consequential hemodynamic derangement. It is not unusual in clinical procedures for the onset of perforation to be heralded by the onset of hemodynamic derangements such as drop in blood pressure. In such cases it is frequently only at that time that the presence of a perforation is recognized. Much time may have elapsed between the creation of a perforation and the subsequent accumulation of enough blood or fluid to create a hemodynamically-significant pericardial effusion or tamponade. Of critical clinical significance is that early detection of such perforation may allow the operator to implement interventions (for example discontinuation of peri-operative anticoagulation) that would mitigate the untoward consequences of pericardial effusion. Retroperitoneal bleeding may lead to hemotoma formation, pain, blood loss, shock, or death. Its detection is frequently only noted after hypotension or other symptoms are noted. Because of the location of blood collection (in the retroperitoneal space) there are usually no other signs commonly associated with bleeding such as hematoma or ecchymosis formation. As in the case of a pericardial effusion prompt recognition offers the opportunity for potentially lifesaving intervention. Another frequent complication of such procedures involves development of blood clots ("thrombosis") within the body of the sheath. These clots may travel ("embolize") via the circulation and lead to necrosis or ischemia of tissue subserved by these blood vessels.

It follows that a method and device which could more rapidly detect the presence of pericardial or retroperitoneal bleeding, prior to the onset of tamponade, is highly desirable. Rapid detection of such blood or fluid accumulation can lead to more timely management—such as aborting the procedure or reversal of the patient's anticoagulation response during such cardiac procedures.

BRIEF SUMMARY

In accordance with at least one embodiment, an apparatus comprises a catheter comprising a first electrode. The apparatus also comprises a second electrode electrically attached to a person and coupled to the first electrode via the person's tissue. Logic is coupled to the electrodes and generates an electrical signal that is provided through the electrodes and computes an impedance or conduction velocity associated with the electrodes based on the electrical signal. The logic stores a threshold against which said computed impedance or conduction velocity is compared by said logic.

A method embodiment comprises coupling a first electrode to a person, coupling a second electrode to the person, and injecting, by a current source, an electrical current that runs through the electrodes. Further, the method comprises computing, by logic, an impedance or conduction velocity based on the injected current, and determining, by the logic, whether the impedance or conduction velocity is at a level indicative of bleeding or a clot. The first and second electrodes, respectively, are placed at sites selected from a group consisting of coronary sinus and esophagus, heart and esophagus, skin and esophagus, coronary sinus and skin, heart and skin, skin and skin, femoral artery and skin, guide wire and skin.

Yet another embodiment comprises an apparatus that includes a catheter comprising a first electrode, a second electrode electrically attached to a person and coupled to the first electrode via the person's tissue, and a signal generator coupled to the electrodes. The signal generator generates an electrical signal that is provided through the electrodes and computes an impedance associated with the electrodes based on the electrical signal.

NOTATION AND NOMENCLATURE

Certain terms are used throughout the following description and claims to refer to particular system components. This document does not intend to distinguish between components that differ in name but not function.

In the following discussion and in the claims, the term "fluid" is defined to include blood and other types of body fluids that may bleed from a vessel or organ and that the disclosed technique detects.

DETAILED DESCRIPTION OF THE PREFERRED EMBODIMENTS

In accordance with preferred embodiments of the invention, a system and method are disclosed herein that involves real-time assessment of resistance or impedance to an electrical signal (current or voltage). Accumulation of sufficient fluid or blood in such areas as the pericardial space leads to changes in both the direct current (DC) resistance and/or the complex impedance to alternating current (AC) current flow. A change in either the resistance or the complex impedance signals fluid accumulation in the space through which the electrical current travels. Embodiments of the invention also use conduction time between two vectors as another variable which may be analyzed. Various embodiments are described herein for measuring impedance to detect fluid bleeding.

Figure 1:
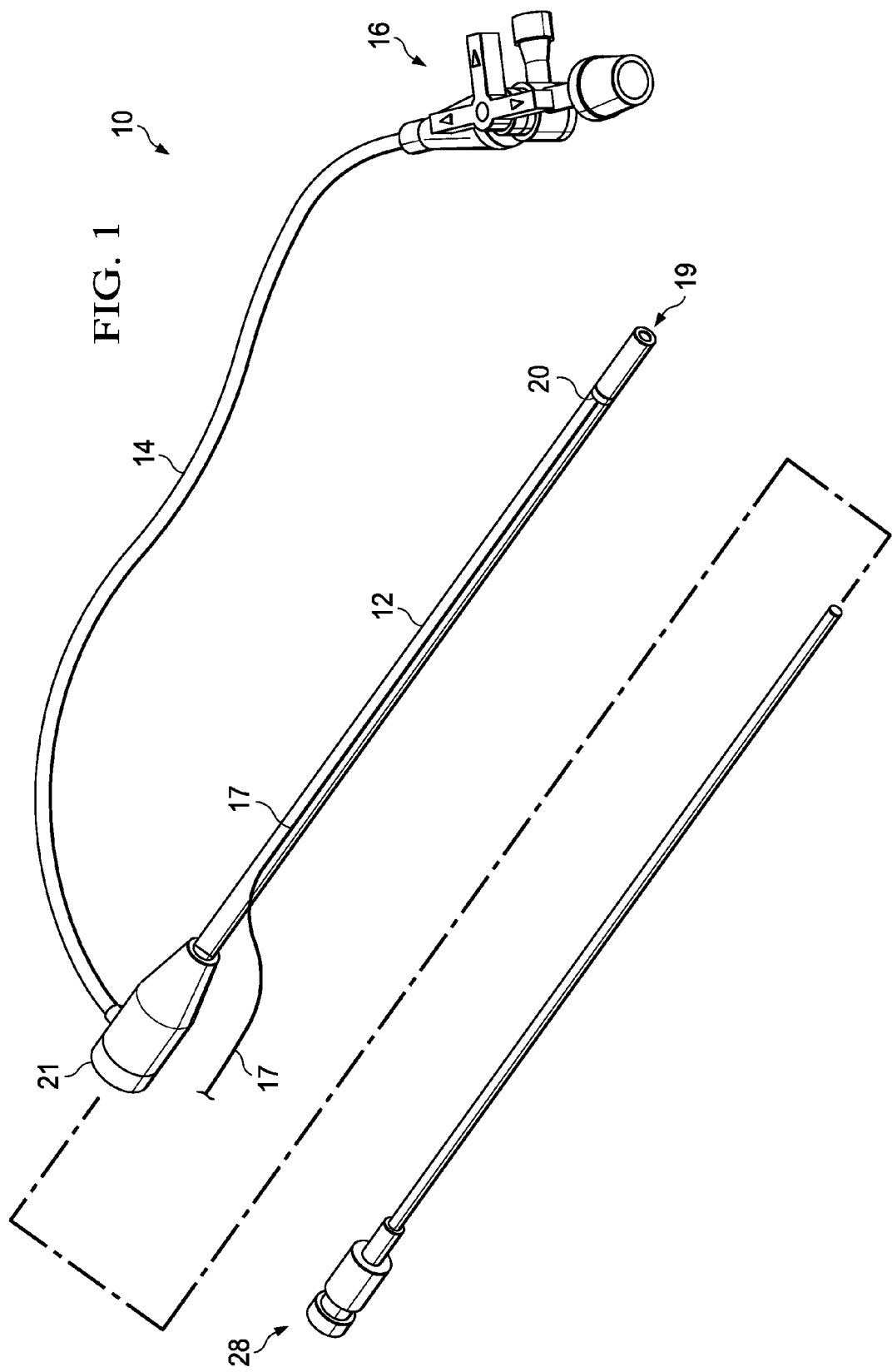
FIG. 1 shows an introducer sheathe with an electrode usable to determine impedance for the detection of bleeding in accordance with various embodiments.

In accordance with one such embodiment, FIG. 1 illustrates an introducer 10 usable to insert a catheter into a blood vessel (vein or artery). The introducer comprises a hollow sheathe 12 having a distal end 19 that is insertable into a blood vessel of a person. The blood vessel may be an artery or a vein. In at least one application, the blood vessel is the femoral artery, but other blood vessels may be used as well. In the illustrative embodiment of FIG. 1, an electrode 20 is provided on the sheathe 12 near distal end 19. The electrode can be provided, however, at other locations along the sheathe 12. As will be explained below, the electrode is usable to measure impedance of the person so as to detect bleeding (e.g., retroperitoneal bleeding). Impedance between pairs of electrodes within the sheath can also be measured to assess the presence of such phenomenona as clots within the sheath.

The sheathe 12 may be coupled to a hub which may or may not incorporate a hemostasis valve 21 from which a side arm 4 may extend that allows to sheathe to be used to administer fluids and or drugs. A valve 16 is provided on the opposing end of the side arm 14. The introducer 10 also includes a dilator 28 that is insertable into the hollow sheathe 12. The dilator and sheathe function to permit a catheter to be inserted into the blood vessel.

Referring still to FIG. 1, an electrical conductor 17 (e.g., a wire) extends along at least part of the sheathe 12 from the electrode 20 and can be connected to an external device (i.e., a device external to the person/patient that receives the sheathe 12). The conductor 17 is usable to conduct signals between the electrode 20 on the sheathe and the external device for impedance measurements.

In FIG. 1, a single electrode 20 is shown on the sheathe 12, but in other embodiments, more than one electrode is provided on the sheathe. Impedances between any individual electrodes may be measured.

Figure 2:
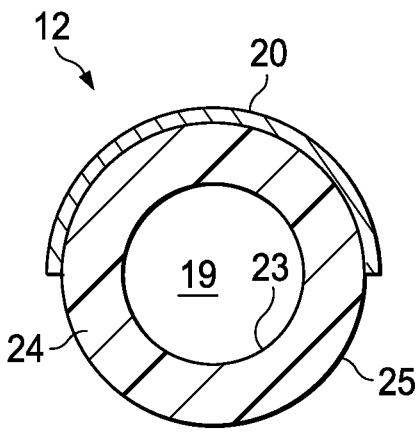
FIG. 2 shows a view of the sheathe with a partial ring electrode on an exterior surface in accordance with various embodiments.

FIGS. 2-5 illustrate various embodiments of the electrode 20. Each figure shows a view of the sheathe facing distal end 19. Referring first to FIG. 2, sheathe 20 comprises material 24 formed as a tubular member and comprising an inner surface 23 and an outer surface 25. In FIG. 1, the electrode 20 comprises a partial ring electrode disposed about a portion of the perimeter of the outer surface 25. In some embodiments, the electrode 20 is adhered (e.g. via glue) to the outer surface 25. In other embodiments, the electrode 20 covers more than 50% of the perimeter of the outer surface 25 and is retained (e.g., clamped) in place like a bracelet.

Figure 3:
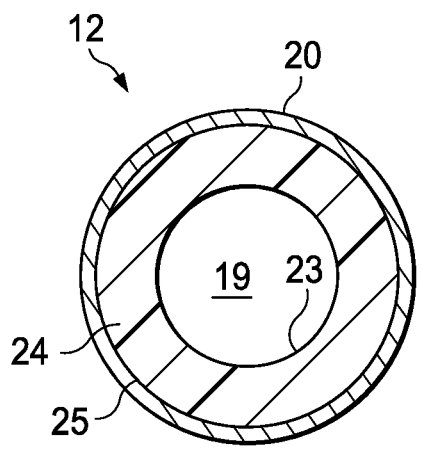
FIG. 3 shows a view of the sheathe with a complete ring electrode on the exterior surface in accordance with various embodiments.

FIG. 3 illustrates an embodiment of the electrode 20 in which the electrode is a complete ring electrode (i.e., completely surrounds the outer surface 25 of the sheathe 12).

Figure 4:
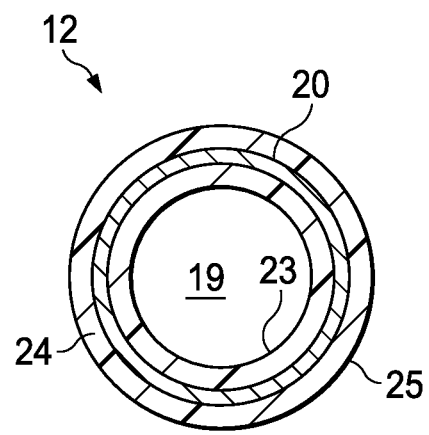
FIG. 4 shows a view of the sheathe with an electrode embedded in the material of the sheathe, in accordance with various embodiments
Figure 5:
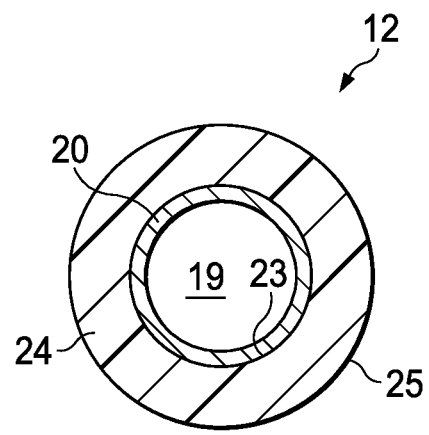
FIG. 5 shows a view of the sheathe with an electrode on an interior surface of the sheathe in accordance with various embodiments.

In FIGS. 2 and 3, the electrode 20 is provided on the outer surface 25 of the sheathe. In FIG. 4, the electrode 20 is embedded within the material 24 of the sheathe in which case the sheathe materials (or at least the segments of the sheath material between the electrodes) must be conductive of electrical signals in the range employed. Furthermore, for the purposes of detection of clot, impedance or conduction between these electrodes may be measured. In FIG. 5, the electrode 20 is provided on the inner surface 23 of the sheathe and thus within the inner hollow portion of the sheathe.

In some embodiments, the electrode 20 is located on the distal end 19 of the sheathe so that the electrode will be inside the blood vessel once the sheathe is inserted into the vessel. In other embodiments, the electrode may be provided on the sheathe at the proximal end outside the blood vessel (and perhaps even outside the person's body). In such embodiments, the electrode 20 preferably is provided on the inner surface of the sheathe (similar to that shown in FIG. 5). Normally, the sheathe is filled with body fluid (e.g., blood).

Figure 6:
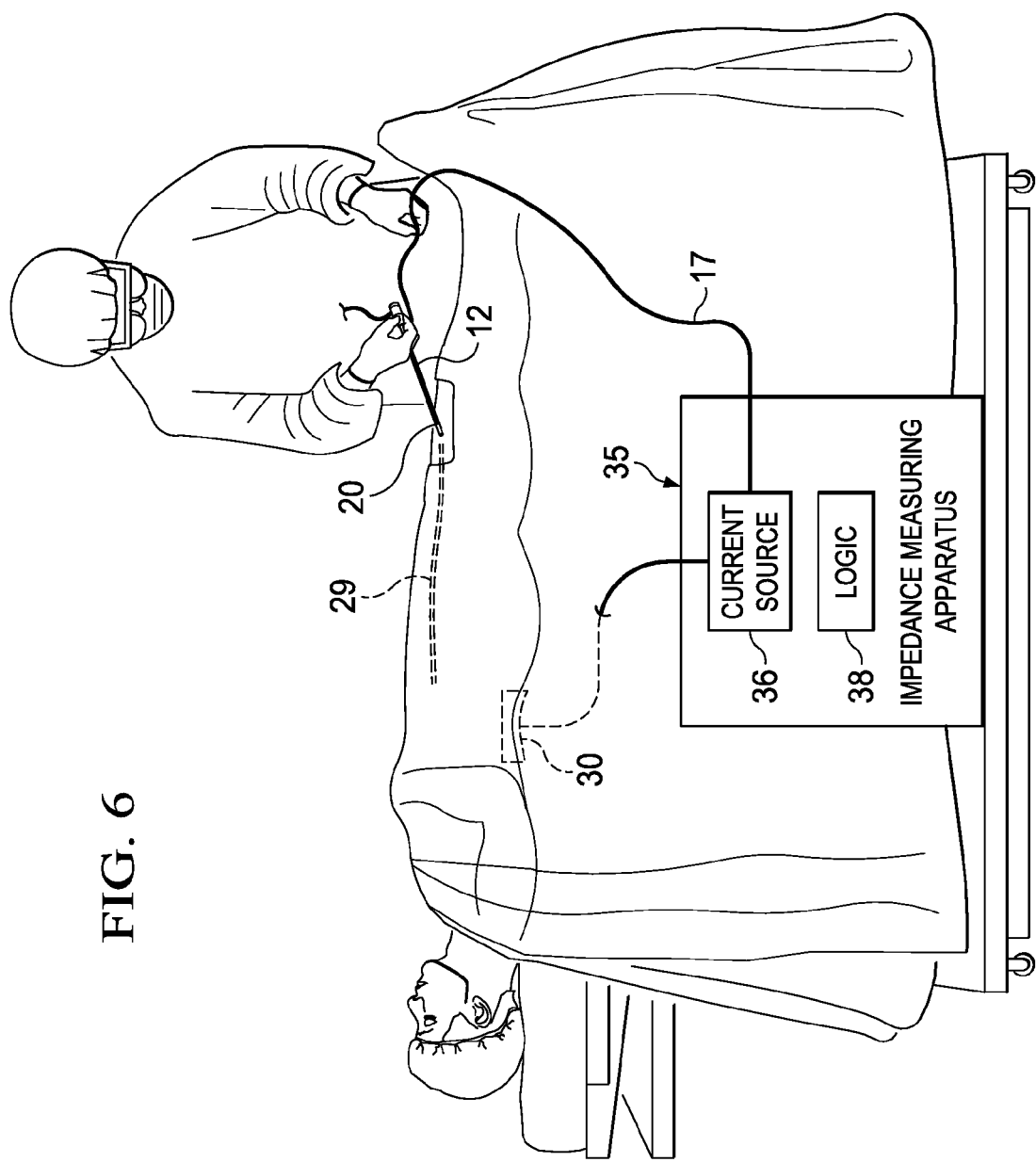
FIG. 6 depicts the sheathe inserted into a blood vessel of person and connected to an impedance measuring apparatus in accordance with various embodiments.

FIG. 6 illustrates a person lying supine with the sheathe 12 inserted into a blood vessel 29. The conductor 17 from the electrode 20 is connected to an impedance measuring apparatus 35. The impedance measuring apparatus 35 comprises a current source 36 and logic 38. The current source 36 may be part of the logic 38 if desired. A second electrode 30 is also connected to the impedance measuring apparatus 35. The current source 36 injects an electrical current through one of the two electrodes 20 or 30. The current then passes through the person's tissues, into the other electrode and back to the current source. The injected current may comprise a series of pulses or a sustained current. The amplitude of the current may be 1 milliamps. If a pulse train is used, the pulse width may be 0.2 milliseconds or less and have a frequency of between 5,000 and 500,000 Hz or higher.

The current source 36 or logic 38 measures the voltage across the electrodes 20, 30 resulting from the current, and computes the ratio of the voltage to current to compute impedance. The impedance is altered in the presence of bleeding and thus can be correlated to bleeding such as retroperitoneal bleeding. The device may also calculate the conduction time between the electrodes. Bleeding will also alter the conduction time between tissues.

The second electrode 30 may be located at any of a variety of locations. The illustrative embodiment of FIG. 6 shows the second electrode 30 attached to the skin on the person's back as a patch electrode. In other embodiments for detecting retroperitoneal bleeding, the second electrode 30 can be attached to a urinary catheter, a rectal temperature probe, an electrosurgical grounding pad, or a patch on lateral aspect of the back as desired.

Figure 7:
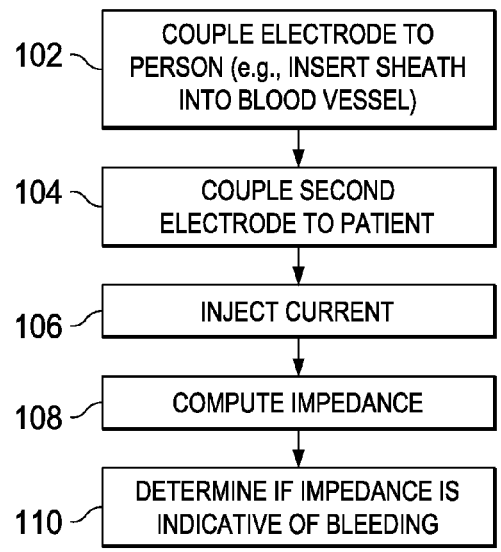
FIG. 7 shows a method in accordance with various embodiments.

FIG. 7 shows an illustrative method. At 102, an electrode is coupled to the person. In the embodiments of FIGS. 1-6, such an electrode is located on an introducer sheathe 12 and coupled to a person as the sheathe is inserted into a blood vessel. At 104, a second electrode is also coupled to the person (e.g., back electrode 30 as shown in FIG. 6). At 106, upon a user activating a control on the impedance measuring device to begin the impedance measuring activity, the impedance measuring apparatus 35 injects current and, at 108, computes the impedance (e.g., measures the voltage and computes the ratio of voltage to current).

At 110, the impedance measuring apparatus 35 determines if the impedance is indicative of bleeding. In some embodiments, the logic 38 of the impedance (or conduction time) measuring apparatus 35 compares the computed impedance to a predetermined threshold, derived threshold based on baseline measurements at the onset of the procedure, otherwise defined acceptable range. The logic 38 determines that bleeding has occurred if the computed impedance or conduction time is outside of the acceptable range for the threshold as previously defined. If bleeding has been detected, the logic 38 may alert a user via an audible and/or visual indicator.

In some embodiments, the impedance measuring apparatus 35 injects a known current and measures the resulting voltage to determine impedance. In other embodiments, the impedance measuring apparatus 35 applies a known voltage to the electrodes and measures the resulting current to determine impedance.

It may be desirable to leave the sheathe 12 in place in the person's blood vessel following the completion of the medical procedure (e.g., RF ablation) for which the sheathe was used in the first place. It is possible that bleeding (e.g., retroperitoneal bleeding) will begin after the completion of the medical procedure. With the sheathe 12 still in place, impedance measurements can be made via the impedance measuring apparatus 35 to detect post-medical procedure completion onset of bleeding. A user of the impedance measuring apparatus can activate a control (e.g., press a button) on the impedance measuring apparatus to activate an impedance/bleed monitoring.

Besides retroperitoneal bleeding, other types of internal bleeding may occur as well. For example, during a catheterization procedure of a patient's heart or surrounding blood vessel(s), bleeding can occur into the pericardial space. In accordance with various embodiments, a catheter includes one or more electrodes, at least one of which is used to make impedance measurements as described above to detect bleeding such as pericardial effusion. In another embodiment of this invention the tip of the catheter or electrode may be located on any guide wire used during coronary intervention (a wire over which a coronary stent or angioplasty apparatus may be advanced is always utilized during such procedures). In this embodiment, the guide wire is or contains an electrode. In such a situation the impedance between the tip of the wire and any second electrode as described elsewhere (such as a skin patch electrode) can be utilized. In another embodiment a distal and proximal electrode (relative to the location of coronary blockage which is to be angioplastied or stented) within the same wire may be used to assess progression of clot formation or perforation and effusion.

Figure 8:
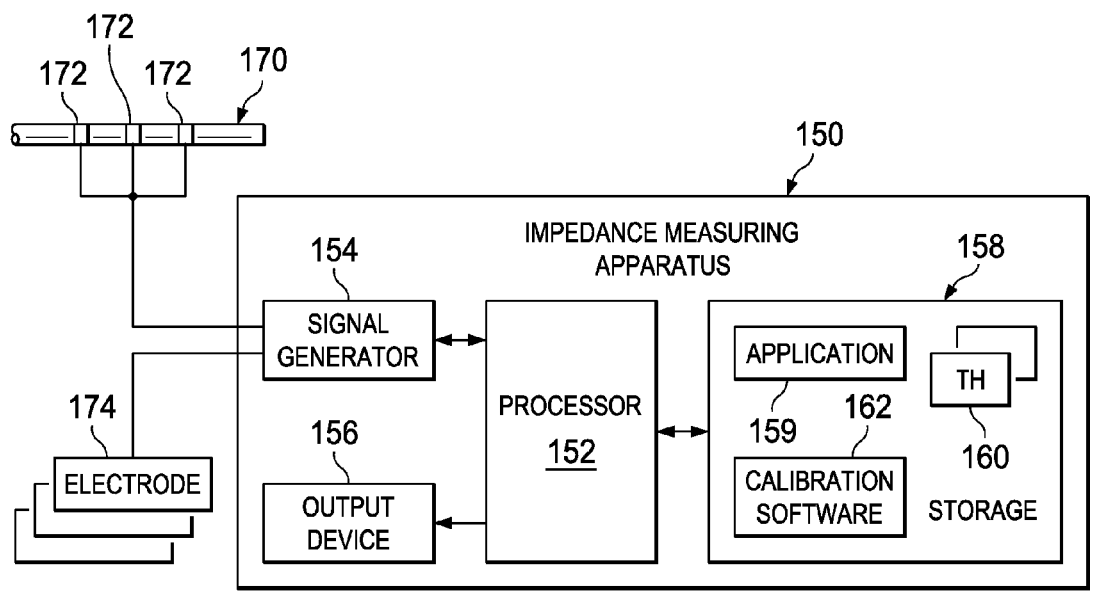
FIG. 8 shows an impedance measuring apparatus in accordance with various embodiments.

FIG. 8 illustrates an embodiment of an impedance measuring apparatus 150 usable to measure impedance and detect bleeding. Any of the attributes described below for impedance measuring apparatus 150 can apply to impedance measuring apparatus 35 of FIG. 6 as well. The impedance measuring apparatus 150 comprises a processor 152, a signal generator 154, an output device 156 and storage 158. The storage 158 comprises volatile memory (e.g., random access memory), non-volatile storage (e.g., read only memory, hard disk drive, Flash storage, etc.), or combinations thereof. The storage 158 comprises an application 159 usable to perform impedance measurements and detect bleeding as described herein and calibration software 162. Both applications 159 and 162 are executed by processor 152. Storage 158 is also used to store one or more impedance thresholds 160. The impedance measuring apparatus 150 comprises logic which includes any combination or all of the processor 152, signal generator 154, and storage 158 (and associated applications and thresholds stored thereon).

Electrodes 172 are provided on a catheter 170 and electrically coupled to the signal generator 154. On or more additional electrodes 174 may also be provided and coupled to signal generator 154. Under control of the processor 152 (via execution of application 159), the signal generator 154 selects one pair of electrodes 172, 174, applies a known current to one of the electrodes in the selected pair, receives the current via the electrode, determines the resulting voltage across the selected pair of electrodes, computes the impedance (ratio of voltage to current), or conduction time and compares the computed impedance or conduction time to a corresponding threshold to determine if bleeding has occurred. A pair of electrodes can be selected coupling two of the electrodes 172, 174 to the signal generator (via a switching device). The signal generator can select two electrodes from among electrodes 172 on the catheter, two electrodes from among electrodes 174, or one electrode each from electrode sets 172 and 174.

If two electrodes 172 are selected on the catheter 170, the impedance measuring apparatus 150 can detect a blood clot within the catheter by measuring the impedance between the two catheter electrodes. The same is true with respect to the embodiment of FIG. 1. The sheathe 12, in some embodiments, comprises more than one electrode 20. The impedance measuring apparatus 35 measures the impedance between the electrodes on the sheathe to detect blood clots that may form within the sheathe.

The catheter 170 can be inserted into any of a variety of veins or arteries. In one embodiment, the catheter 170 is inserted into the femoral artery (for detection, for example, of retroperitoneal effusion), the heart or coronary vasculature such as the coronary sinus (for detection of pericardial effusion), or other blood vessels or anatomic structures. The coronary sinus is an epicardial vein through which venous drainage of coronary circulation occurs. It is on the inferior surface of the left atrium. More distally this structure turns into the great cardiac vein or any of its other tributaries.

The electrodes 174 may be located at any of variety of sites. An electrode 174, for example, may be located on the person's esophagus, on the person's skin, or on the person's heart. Moreover, impedance can be measured for detecting bleeding between, for example, the coronary sinus and skin, coronary sinus and esophagus, skin and skin (e.g., patient's front and back), heart and coronary sinus, heart and esophagus, two sites on the same catheter, two sites on the same sheathe, two sites on the same vein and femoral artery to skin.

As explained herein, more than two electrodes can be used for measuring impedance. Impedance can be measured between any pair of electrodes and such an impedance measurement represents a vector. For example, in a three-electrode system (first, second, and third electrodes), there are three possible impedance vectors including the impedance between the first and second electrodes, the impedance between the first and third electrodes, and the impedance between the second and third electrodes. The number of vectors increases disproportionately with increasing numbers of electrodes. The physical location of the various electrodes may be useful to detect bleeding in different locations. For example, bleeding may occur between the first and second electrodes, but the fluid (e.g., blood) may not be present between the second and third electrodes. Thus, in this example, the impedance vector associated with the first and second electrodes may be indicative of the bleed, but not so the impedance vector associated with the second and third electrodes or possibly the first and third electrodes. Moreover, more than two electrodes provides an enhanced ability to detect bleeding in different locations than might be possible in a two-electrode only system.

In some embodiments, the computed impedance may be resistance while in other embodiments, the computed impedance is complex having both amplitude and phase components. In other embodiments the computed variable is conduction velocity. Further, the impedance measuring apparatus 150 (or impedance measuring apparatus 35 in FIG. 6) determines and stores an impedance threshold for each impedance vector. Two or more of the various impedance thresholds may be the same or the impedance thresholds may all be different. Each impedance threshold may be an amplitude only value (resistance) or, in the case of complex impedance, comprise an amplitude value and a phase value.

Figures 9, 10:
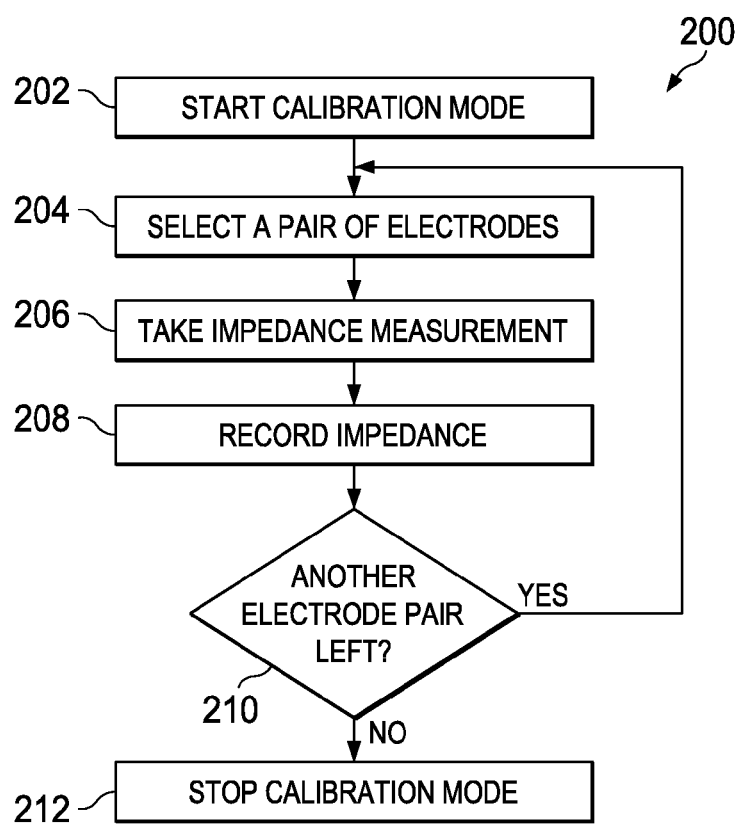
FIG. 9 illustrates various impedance thresholds stored in the impedance measuring apparatus.
FIG. 10 depicts an illustrative method of calibrating the impedance measuring apparatus.

FIG. 9 illustrates the thresholds 160 as a table comprising one or more vectors A, B, C, etc. Each vector represents a pair of electrodes. For each vector, there is an amplitude threshold value 166 and/or a phase threshold value 168. In some embodiments, the impedance measuring apparatus detects the presence of bleeding if either of the amplitude or phase of the computed impedance for a given vector exceeds its corresponding amplitude or phase value. In other embodiments, the impedance measuring apparatus detects a bleed only if both the computed amplitude and phase exceed their corresponding threshold counterparts. The threshold counterparts may have been derived in a variety of ways one of which may be baseline measurements at the beginning of the procedure for each individual patient as explained below.

FIG. 10 illustrates a method 200 for calibrating the impedance measuring apparatus (35 or 150) for the various thresholds. In some embodiments, the impedance measuring apparatus comprises a calibration mode that can be initiated by a user of the impedance measuring apparatus (e.g., by pressing a button). The processor of the impedance measuring apparatus executes the calibration software 162 (impedance measuring apparatus 35 may also have similar software to be executed by a processor). FIG. 10 is a method performed by the process upon executing the calibration software 162. The calibration mode is performed preferably before the medical procedure [e.g., coronary angiography (after the wire has been placed through the blockage but before angioplasty) or electrophysiology study (after catheters have been placed in the coronary sinus but before delivery of radiofrequency ablation)] begins.

The calibration mode begins at 202. A pair of electrodes is selected at 204 and at 206 and 208, an impedance measurement is taken and the computed impedance is recorded (e.g., stored in storage 158) (as amplitude and/or phase values). Preferably, the impedance measurement for a selected pair of electrodes is taken over the course of several breaths by the patient. The impedance computed for the selected impedance vector will vary during a respiratory cycle. By taking the impedance measurement over the course of several breaths (e.g., 10 seconds), the impedance measuring apparatus can account for the normal variations in impedance. The threshold (amplitude or phase) may be computed as an average during the recording period or may be set as the peak value detected (or a value slightly higher (e.g., 5% higher) than the peak). At 210, the impedance measuring apparatus determines whether there is an additional impedance vector for which a threshold is to be determined. If there is, control loops back to step 204 at which such an electrode pair is selected. If not more electrode pairs are to be selected, than the calibration mode stops at 212. This calibration process may take several minutes. The same calibration variables may be measured for conduction velocities.

Once the calibration process is completed, the medical procedure (which might result in bleeding or clot formation) can begin. Any bleeding will be detected a change in impedance above deviating from an impedance threshold (e.g., an increase above the threshold or decrease below the threshold).

The impedance measuring techniques described herein to detect bleeding are also usable to detect a hemothorax. In this application, electrode locations would include the anterior chest and posterior chest walls, the esophagus at the level near the heart, the trachea, as well as numerous intravascular and intra-cardiac and intra-coronary locations. The electrodes may be on catheters or wires.

With regards to conduction velocity, the logic (e.g., that contained in the measuring devices described herein) assesses the conduction time between the onset of the electrical impulse in the first (transmitting) electrode and second (receiving) electrode. These electrodes are identical to the electrodes described in this invention. The electrical output is in the same range with regards to frequency and amplitude. The measured variable, however is the difference (delta) in time (usually milliseconds) between onset of stimulus (electrical output) in the transmitting electrode and sensing of that impulse (electrical sensing) in the receiving electrode. Conduction velocity is heterogeneous with variations in tissue characteristic. As fluid develops, the conduction velocity between the transmitting and receiving electrode will also change. This will be noted as a deviation from a baseline values (similar to the impedance values/thresholds described herein). An alert will then be issued. The various embodiments of apparatus and methods described above can also be used to measure conduction velocity and use conduction velocity to determine thickening of the heart and the presence of fluid bleeding.

While the embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference in the Background Information is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. An apparatus, comprising:
an introducer usable to insert a catheter in to a blood vessel, the catheter comprising a first electrode;
a second electrode when electrically attached to a person is to be coupled to said first electrode via the person's tissue; and
logic coupled to said electrodes, said logic generates an electrical signal that is provided through said electrodes and computes an impedance or conduction velocity associated with said electrodes based on said electrical signal;
wherein said logic stores a threshold against which said computed impedance or conduction velocity is compared by said logic; and
wherein said logic detects bleeding based on a comparison of the computed impedance or conduction velocity to the threshold and generates an alert indicative of the patient bleeding based on the computed impedance or conduction velocity exceeding the threshold.

2. The apparatus of claim 1 comprising a third electrode and said logic computes impedances between said first and third electrodes and said second and third electrodes, said logic also stores separate thresholds against which said impedances are compared.

3. The apparatus of claim 2 wherein the logic implements a calibration mode in which said thresholds are determined, said calibration mode initiated before a medical procedure is begun.

4. The apparatus of claim 3 wherein, while in the calibration mode, the logic determines an impedance between each pair of the first, second, and third electrodes.

5. The apparatus of claim 1 wherein the logic implements a calibration mode in which said threshold is determined, said calibration mode initiated before a medical procedure is begun.

6. The apparatus of claim 1 wherein the threshold comprises an impedance amplitude value.

7. The apparatus of claim 1 wherein the threshold comprises an impedance phase value.

8. The apparatus of claim 1 wherein the threshold comprises an impedance phase value and an impedance amplitude value.

9. The apparatus of claim 1 wherein when the catheter is inserted into the coronary sinus of the e son said logic computes said impedance with the catheter inserted into the coronary sinus of the person.

10. The apparatus of claim 1 wherein when the second electrode is electrically attached to the person, the second electrode is electrically attached at a site selected from a group consisting of the person's skin, the person's esophagus, and the person's heart.

11. An apparatus, comprising:
an introducer usable to insert a catheter in to a blood vessel, the catheter comprising a first electrode;
a second electrode when electrically attached to a person is to be coupled to said first electrode via the person's tissue; and
a signal generator coupled to said electrodes, said signal generator generates an electrical signal that is provided through said electrodes, computes an impedance associated with said electrodes based on said electrical signal, and determines whether the person is experiencing bleeding based on the computed impedance;
wherein the signal generator generates an alert based on a determination that the person is experiencing bleeding.

12. The apparatus of claim 11 wherein the catheter comprises a plurality of electrodes which are selectable by the signal generator to compute impedance.

* * * * *